(12) United States Patent
Peng et al.

(10) Patent No.: US 12,318,369 B2
(45) Date of Patent: *Jun. 3, 2025

(54) ANALGESIC AND ANTIPRURITIC PHARMACERTICAL COMPOSITION AND APPLICATION THEREOF

(71) Applicant: KEVICI (SHANGHAI) PHARMACEUTICAL CO., LTD., Shanghai (CN)

(72) Inventors: Changgeng Peng, Chengdu (CN); Liting Sun, Chengdu (CN); Ruilong Xia, Chengdu (CN)

(73) Assignee: KEVICI (SHANGHAI) PHARMACEUTICAL CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/590,910

(22) Filed: Feb. 28, 2024

(65) Prior Publication Data

US 2024/0197690 A1    Jun. 20, 2024

Related U.S. Application Data

(63) Continuation of application No. 18/171,431, filed on Feb. 20, 2023, now Pat. No. 11,938,118, which is a continuation of application No. PCT/CN2021/072071, filed on Jan. 15, 2021.

(30) Foreign Application Priority Data

Aug. 20, 2020    (CN) .......................... 202010845095.2

(51) Int. Cl.
| | | |
|---|---|---|
| *A01N 43/00* | (2006.01) | |
| *A01N 43/46* | (2006.01) | |
| *A61K 31/4164* | (2006.01) | |
| *A61K 31/427* | (2006.01) | |
| *A61K 31/55* | (2006.01) | |
| *A61K 47/02* | (2006.01) | |
| *A61K 47/36* | (2006.01) | |
| *A61P 25/04* | (2006.01) | |

(52) U.S. Cl.
CPC ........ *A61K 31/427* (2013.01); *A61K 31/4164* (2013.01); *A61K 47/02* (2013.01); *A61K 47/36* (2013.01); *A61P 25/04* (2018.01)

(58) Field of Classification Search
None
See application file for complete search history.

(56) References Cited

FOREIGN PATENT DOCUMENTS

WO    2010079443 A1    7/2010
WO    2017075222 A1    5/2017

OTHER PUBLICATIONS

International Search Report in PCT/CN2021/072071 mailed on Apr. 28, 2021, 8 pages.
Written Opinion in PCT/CN2021/072071 mailed on Apr. 28, 2021, 8 pages.
Alexandros H. Kanellopoulos et al., Voltage-gated sodium channels and pain-related disorders, Clinical Science, 130: 2257-2265, 2016.
Helen Kühn et al., Complementary roles of murine Nav1.7, Nav1.8 and Nav1.9 in acute itch signaling, Scientific Reports, 2020, 12 pages.
Danica Jurcakova et al., Voltage-Gated Sodium Channels Regulating Action Potential Generation in Itch-, Nociceptive-, and Low-Threshold Mechanosensitive Cutaneous C-Fibers, Molecular Pharmacology, 94: 1047-1056, 2018.
Aoibhinn McDonnell et al., Efficacy of the Nav1.7 blocker PF-05089771 in a random, placebo-controlled, double-blind clinical study in subjects with painful diabetic peripheral neuropathy, Pain, 159(8): 1465-1476, 2018.
Jonathan W. Theile et al., The Selective Nav1.7 Inhibitor, PF-05089771, Interacts Equivalently with Fast and Slow Inactivated Nav1.7 Channels, Molecular Pharmacology Fast Forward, 2016, 37 pages.
Nigel Alan Swain et al., Discovery of Clinical Candidate 4-[2-(5-Amino-1H-pyrazol-4-yl)-4-chlorophenoxy]-5-chloro-2-fluoro-N-1,3-thiazol-4-ylbenzenesulfonamide (PF-05089771): Design and Optimization of Diaryl Ether Aryl Sulfonamides as Selective Inhibitors of NaV1.7, Journal of Medicinal Chemistry, 2017, 14 pages.

(Continued)

*Primary Examiner* — Layla Soroush
(74) *Attorney, Agent, or Firm* — POSEIDON ADVANCED IP LLC

(57) ABSTRACT

An analgesic and antipruritic pharmaceutical composition, including PF-05089771 shown as

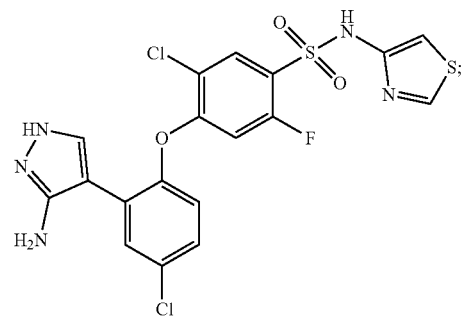

and PF-04885614 shown as

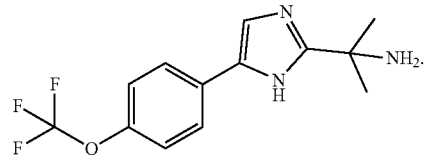

An application of the analgesic and antipruritic pharmaceutical composition in the treatment of a disease in which both a voltage-gated sodium channel 1.7 ($Na_v1.7$) and a voltage-gated sodium channel 1.8 ($Na_v1.8$) are involved.

20 Claims, 10 Drawing Sheets

(56) References Cited

OTHER PUBLICATIONS

Jonathan Theile et al., Nav1.7 Inhibitor, PF-05089771, Inhibits Fast- and Slow-Inactivated Channels with Similar Affinities, Biophysical Journal: 59th Annual meeting of the Biophysical-Society, 2015, 2 pages.

Sooyeon Jo et al., Lidocaine Binding Enhances Inhibition of Nav1.7 Channels by the Sulfonamide PF-05089771, Molecular Pharmacology, 97: 377-383, 2020.

Pieter Siebenga et al., Lack of Detection of the Analgesic Properties of PF-05089771, a Selective Nav 1.7 Inhibitor, Using a Battery of Pain Models in Healthy Subjects, Clinical and Translational Science, 13: 318-324, 2020.

Alan D. Brown et al., The discovery and optimization of benzimidazoles as selective NaV1.8 blockers for the treatment of pain, Bioorganic & Medicinal Chemistry 27: 230-239, 2019.

ANALGESIC AND ANTIPRURITIC PHARMACERTICAL COMPOSITION AND APPLICATION THEREOF

CROSS-REFERENCE TO RELATED APPLICATIONS

This application is a continuation of U.S. application Ser. No. 18/171,431 filed on Feb. 20, 2023, which is a continuation of International Patent Application No. PCT/CN2021/072071, filed on Jan. 15, 2021, which claims the benefit of priority from Chinese Patent Application No. 202010845095.2, filed on Aug. 20, 2020. The content of the aforementioned application, including any intervening amendments thereto, is incorporated herein by reference in its entirety.

TECHNICAL FIELD

This application relates to medicinal chemistry, and more particularly to an application of voltage-gated sodium channel 1.7 (Nav1.7) inhibitor and voltage-gated sodium channel 1.8 (Nav1.8) inhibitor in treating diseases caused by hyperactive Nav1.7 and Nav1.8.

BACKGROUND

Neuropathic pain is a chronic pain. Currently, the commonly-used clinical drugs such as Gabapentin and Pregabalin can only alleviate the neuropathic pain of 40%-60% of the patients, accompanied by sedation effects (such as drowsiness, fatigue and dizziness). Consequently, it is urgently required to develop more effective drugs to alleviate the chronic pain of the patients. Voltage-gated sodium channels 1.7 and 1.8 (Nav1.7 and Nav1.8) are predominately expressed in peripheral sensory neurons, and play an important role in the itch and pain transmission and transduction. The Nav is a transmembrane glycoprotein complex including one a subunit and several β subunits. For instance, gain-of-function mutations of SCN9A encoding the a subunit of Nav1.7 will cause inherited erythromelalgia and idiopathic small fiber neuropathies (SFN), whereas the loss of function of mutations of SCN9A leads to congenital insensitivity to pain in human, and the knock-out of Nav1.7 mice are free to all kinds of pain (including inflammatory pain and neuropathic pain). Gain-of-function mutations of SCN10A encoding a subunit of Nav1.8 are involved in small fiber neuropathies (SFN), neuropathic pain and diabetic peripheral neuropathy, while the loss-of-function mutation of SCN10A was found in human with lower mechanical pain sensitivity and SCN10A-null mice have higher threshold to noxious mechanical stimuli and heat stimuli (A. Kanellopoulos et al., Voltage-gated sodium channels and pain-related disorders. Clin Sci (Lond). 2016 Dec. 1; 130(24): 2257-2265). Also, the gene knockout experiments confirmed that Nav1.7 and Nav1.8 are necessary for the itch conduction, indicating that Nav1.7 and Nav1.8 are potential targets for the treatment of itch (H. Kühn et al., Complementary roles of murine Nav1.7, Nav1.8 and Nav1.9 in acute itch signaling. Sci Rep. 2020 Feb. 11; 10(1):2326.). It has been recently reported that Nav1.7 and Nav1.8 were co-expressed in some nociceptive neurons of the dorsal root ganglia (DRG), and it is necessary to inhibit the activities of both Nav1.7 and Nav1.8 simultaneously to inhibit the action potential generation of these nociceptive neurons. (D. Jurcakova et al., Voltage-Gated Sodium Channels Regulating Action Potential Generation in Itch-, Nociceptive-, and Low-Threshold Mechanosensitive Cutaneous C-Fibers. Mol Pharmacol. 2018 94, 1047-1056). Thus, it is speculated that a better pain relieve effect may be reached by simultaneously inhibiting the functions of Nav1.7 and Nav1.8.

Despite extensive efforts in exploring and developing Nav1.7 selective small-molecule inhibitors and Nav1.8 selective small-molecule inhibitors, none has yet been successful for the clinical application. Two available selective Nav1.7 inhibitors PF-05089771 and GNE-0439 and two available selective Nav1.8 inhibitors PF-04885614 and PF-04531083 are structurally shown as follows:

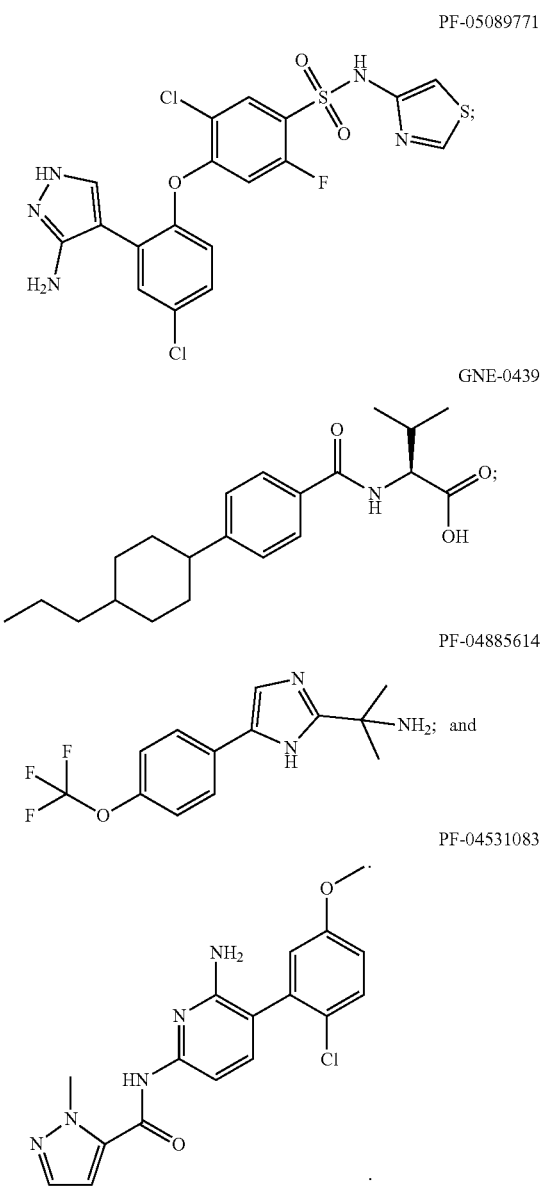

The IC50 of PF-05089771 for inhibiting the human Nav1.7 is 11 nM, but this compound fails to be used in the treatment of diabetic neuropathic pain due to the poor efficacy. (A. McDonnell., Efficacy of the Nav1.7 blocker PF-05089771 in a randomised, placebo-controlled, double-blind clinical study in subjects with painful diabetic peripheral neuropathy. Pain. 2018 August; 159(8):1465-1476.).

Additionally, reasons for the poor analgesic effect of PF-05089771 in vivo is unclear.

SUMMARY

It has been found that the analgesic effect produced by inhibiting the activity of Nav1.7 or Nav1.8 alone weakens with the duration of peripheral nerve injury, and the neuropathic pain mice, which have poor response to the Nav1.7 small-molecule inhibitors, show better response to the Nav1.8 small-molecule inhibitors. Based on these results, analgesic effects produced by the combined administration of different Nav1.7 inhibitors and Nav1.8 inhibitors are investigated, and the results demonstrate that the combined administration of appropriate doses of Nav1.7 inhibitor PF-05089771 and Nav1.8 inhibitor PF-04885614 can significantly enhance the analgesic effect and improve the individual response rate to 100%. Thus, a pharmaceutical composition containing PF-05089771 and PF-04885614 is provided herein for the treatment of diseases involving Nav1.7 and Nav1.8 activity, including but not limited to, chronic pain and pruritus.

Technical solutions of this application are described as follows.

This application provides an analgesic and antipruritic pharmaceutical composition, comprising:

PF-05089771 shown as

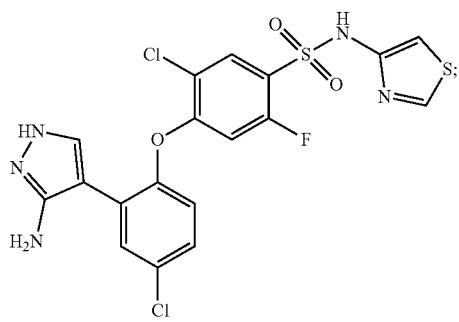 [SMILES: Nc1n[nH]cc1-c1cc(Cl)ccc1Oc1cc(F)c(S(=O)(=O)Nc2cscn2)cc1Cl]

and
PF-04885614 shown as

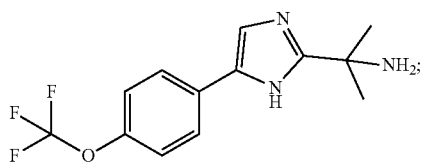 [SMILES: CC(C)(N)c1ncc(-c2ccc(OC(F)(F)F)cc2)[nH]1]

wherein the analgesic and antipruritic pharmaceutical composition is configured to treat a disease in which both a voltage-gated sodium channel 1.7 (Nav1.7) and a voltage-gated sodium channel 1.8 (Nav1.8) are involved.

In an embodiment, the disease comprises pruritus and pain; wherein the pain is inflammatory pain, neuropathic pain or a combination thereof; the inflammatory pain is selected from the group consisting of postoperative and traumatic pain, musculoskeletal pain, menalgia, visceralgia and a combination thereof; the musculoskeletal pain comprises arthralgia; and the neuropathic pain is selected from the group consisting of hemicrania, odontalgia, trigeminal neuralgia, cancer-related pain, postherpetic pain, pain after spinal cord injury, sciatica, diabetic peripheral neuropathy pain and a combination thereof.

In an embodiment, a weight ratio of the PF-05089771 to the PF-04885614 is (100-1):(1-100), preferably (50-1):1, and more preferably (20-30):1.

In an embodiment, an administration route of the analgesic and antipruritic pharmaceutical composition comprises oral administration, intraoral administration, injection, respiratory administration, cutaneous administration, ophthalmic administration, nasal mucosal administration, rectal administration, vaginal administration, otic administration and dialysis.

In an embodiment, the analgesic and antipruritic pharmaceutical composition further comprises a pharmaceutically-acceptable carrier; wherein the pharmaceutically-acceptable carrier is a solvent, an excipient, a dispersion medium, a coating, an iso-osmotic solution, a slow-release agent or a combination thereof.

In an embodiment, the pharmaceutically-acceptable carrier is selected from the group consisting of starch, microcrystalline cellulose, lactose, sucrose, mannitol, inorganic salt, hydroxypropyl cellulose, sodium carboxymethyl starch, cross-linked polyvinylpyrrolidone, sodium alginate, agar, hydroxypropyl methyl cellulose, methylcellulose, hydroxyethyl cellulose, Carbopol, polyvinyl alcohol, acrylic resin, chitosan, beeswax, stearic acid and a combination thereof; and the inorganic salt is selected from the group consisting of calcium sulfate, calcium hydrogen phosphate, calcium carbonate, calcium sulphate dihydrate and a combination thereof.

DETAILED DESCRIPTION

As is well known in the art, voltage-gated sodium channels (Navs) play an important role in the itch and pain transmission. Sodium channel 1.7 (Nav1.7) and sodium channel 1.8 (Nav1.8) are involved in the itch and pain transmission under physiological and pathological conditions.

It has been observed from the investigation on the role of Nav1.7 and Nav1.8 in SNI-induced neuropathic pain mice that as the time course of the disease prolonged, the analgesic effect of Nav1.7 inhibitor PF-05089771 and Nav1.8 inhibitor PF-04885614 significantly diminished, and the individual response rate also decreased. In addition, individuals who showed a poor response to PF-05089771 had a good response to PF-04885614. Thus, the therapeutic effect of Nav1.7 inhibitor in combination with Nav1.8 inhibitor on chronic neuropathic pain was studied, and the results demonstrated that there was synergistic analgesic effect on chronic neuropathic pain when combining PF-05089771 with PF-04885614 in different dose ratios, and the individual response rate was improved. The combined administration of PF-05089771 and PF-04885614 at the optimal dose brought not only an obvious analgesic effect, but also a high response rate (up to 100%). However, there was no synergistic effect between GNE-0439 and PF-04885614. Though the combined use of PF-05089771 and PF-04531083 showed a synergistic analgesic effect, it was observed that the effective dose of PF-04531083 was also accompanied by obvious side effects such as sedation and weight loss. Therefore, it was concluded that the combined use of PF-05089771 and PF-04885614 can significantly relieve the neuropathic pain, and the efficacy was superior to the single use of PF-05089771 or PF-04885614. Under the optimal dose, the combination of PF-05089771 and PF-04885614 exerted an analgesic effect equivalent to the clinical drug Gabapentin, and had no side effects (such as sedation) which occurred in the case of administering the equivalent dose of Gabapentin.

This application will be described in detail below with reference to the accompanying drawings and embodiments.

Example 1

The efficacy of individual inhibitors used alone was tested herein.

Figure 1:
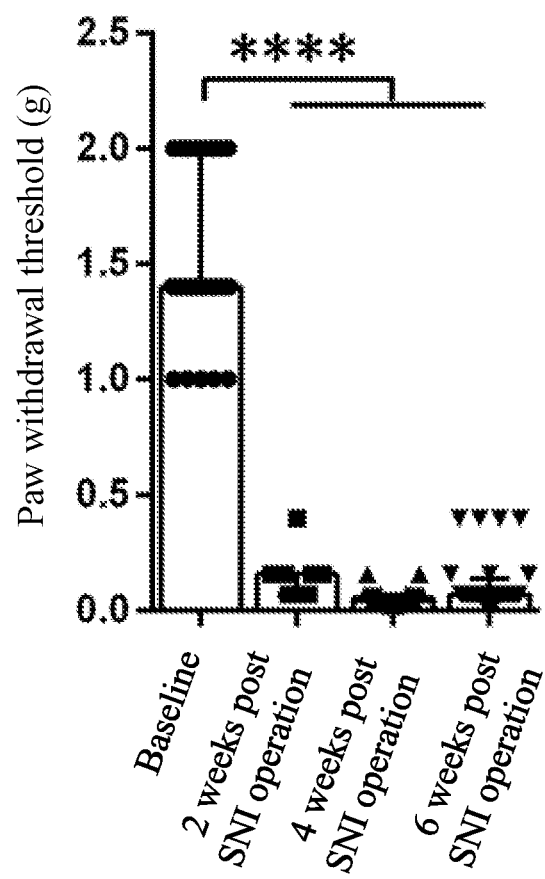
FIG. 1 illustrates comparison of paw withdrawal thresholds (PWT) of mice before and after spared nerve injury (SNI) operation in Example 1, where the PWTs of mice at 2 weeks, 4 weeks and 6 weeks post operation are significantly lower than the baseline threshold (n=20-28, ****P<0.0001, with Mann-Whitney test)

The relieve effect of Nav1.7 inhibitor and Nav1.8 inhibitor on SNI-induced neuropathic pain at different time points was investigated. C57/BJ6 mice aged 5-6 weeks were purchased from Shanghai SLAC Laboratory Animal Co., Ltd and fed for 6 months. After that, the mice were placed in a transparent plexiglass chamber on an iron support. 30 minutes later, the baseline mechanical threshold (paw withdrawal threshold, PWT) of the mice was detected by Von Frey (DanMicGlobal, CA, USA). The average threshold of the mice was 1.54+0.07 g (see FIG. 1). The spared nerve injury (SNI)-induced neuropathic pain C57/BJ6 mouse model was established according to Pertin, M et al (Pertin, M., Gosselin, RD., Decosterd, I. (2012). The Spared Nerve Injury Model of Neuropathic Pain. In: Luo, Z. (eds) Pain Research. Methods in Molecular Biology, vol 851. Humana Press). The SNI-induced neuropathic pain mice were measured for the mechanical pain threshold using Von Frey respectively at 2 weeks, 4 weeks and 6 weeks post operation. The results were presented in FIG. 1, from which it can be observed that the thresholds post operation were significantly lower than the baseline threshold, and the means of threshold at 2 weeks, 4 weeks and 6 weeks post operation were 0.14+0.02 g, 0.06+0.01 g, and 0.12+0.02 g, respectively. Further, the analgesic effect of intraperitoneal injection of 2 mg/kg PF-05089771 (Nav1.7 inhibitor, Bio-Techne) or 45 µg/kg PF-04885614 (Nav1.8 inhibitor, Bio-Techne) on SNI mice respectively at 2 weeks, 4 weeks, and 6 weeks post operation was analyzed.

Figure 2:
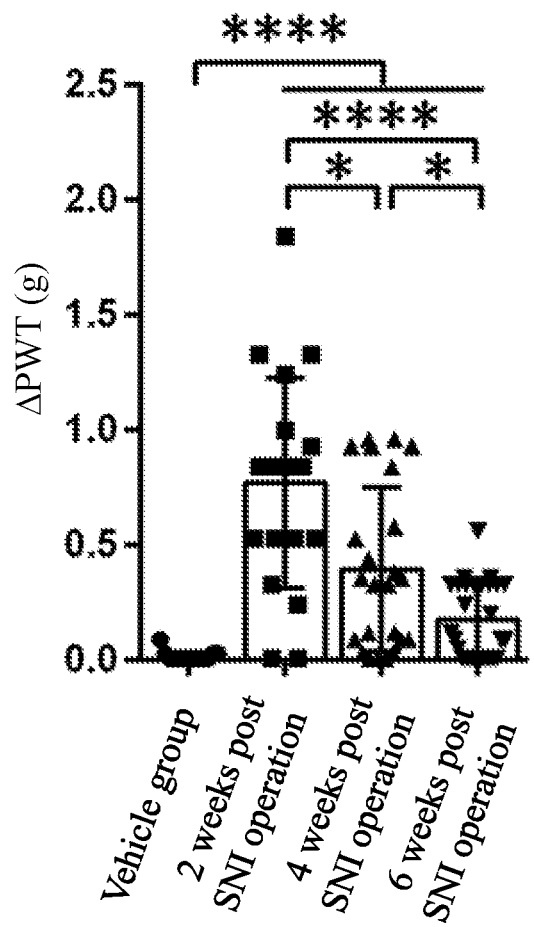
FIG. 2 demonstrates an analgesic effect (expressed by APWT) of intraperitoneal injection of 2 mg/kg PF-05089771 (Nav1.7 inhibitor) in SNI mice in Example 1, where the analgesic effect gradually decreases from 2 weeks to 6 weeks post operation (n=20-28, *P<0.05, ****P<0.0001, with Mann-Whitney test)

The mechanical pain threshold of mice was tested 1 hour after injection. The results showed that the injection of 2 mg/kg PF-05089771 could significantly relieve neuropathic pain in SNI mice at 2 weeks post operation, and increase the mechanical pain threshold by 0.77+0.10 g ($\Delta$PWT=post-administration threshold—pre-administration threshold). Among them, the mice with poor response ($\Delta$PWT≤ 0.2 g) accounted for 10% (2/20) of all tested mice. However, the efficacy of 2 mg/kg PF-05089771 gradually decreased with the extension of time post operation. At 4 weeks post operation, the mechanical pain threshold of mice could only be increased by 0.39+0.07 g, and the mice with poor response ($\Delta$PWT≤0.2 g) accounted for 41.7% (10/24); and at 6 weeks post operation, the mechanical pain threshold of mice could only be slightly increased by 0.17+0.03 g, and the proportion of mice with poor response ($\Delta$PWT≤ 0.2 g) rose to 57.1% (16/28), as shown in FIG. 2.

Figure 3:
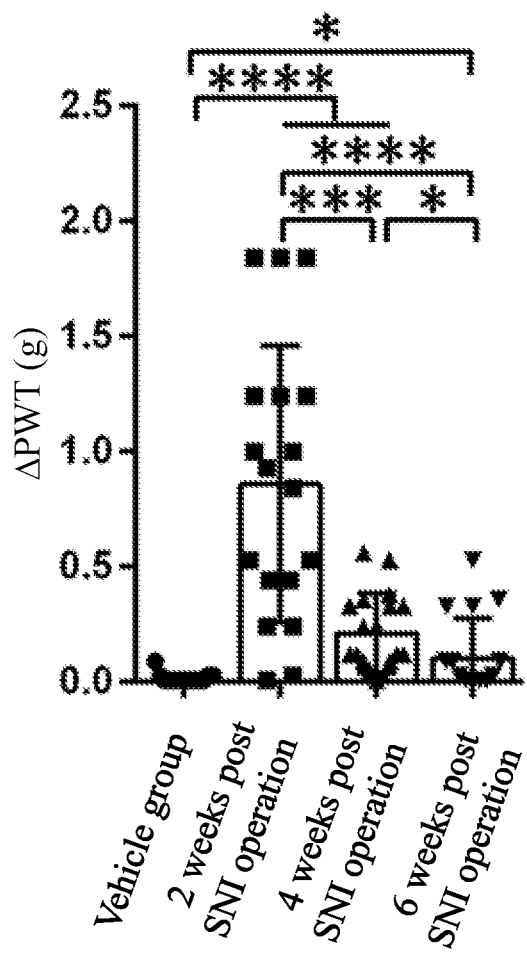
FIG. 3 demonstrates an analgesic effect of intraperitoneal injection of 45 µg/kg PF-04885614 (Nav1.8 inhibitor) in SNI mice in Example 1, where the analgesic effect gradually decreases from 2 weeks to 6 weeks post operation (n=17-21, *P<0.05, *P<0.001, **P<0.0001, with Mann-Whitney test)

Similar to PF-05089771, the injection of 45 µg/kg PF-04885614 can also significantly relieve the neuropathic pain in SNI mice at 2 weeks post operation, and elevate the mechanical pain threshold by 0.86+0.14 g. Moreover, the mice with poor response ($\Delta$PWT≤ 0.2 g) accounted for 11.1% (2/18). However, the efficacy of 45 µg/kg of PF-04885614 sharply diminished over time post operation. At 4 weeks post operation, the mechanical pain threshold of mice was only improved by 0.21+0.04 g, and there was no statistically significant difference compared with the control group. Additionally, the mice with poor response ($\Delta$PWT≤0.2 g) accounted for 52.6% (10/19). At 6 weeks post operation, the mechanical pain threshold was only improved by 0.10+0.04 g, and the mice with poor response (ΔPWT≤0.2 g) accounted for 76.5% (13/17), as shown FIG. 3.

Example 2

In this example, the efficacy of a combined administration of inhibitors was investigated.

Figure 4:
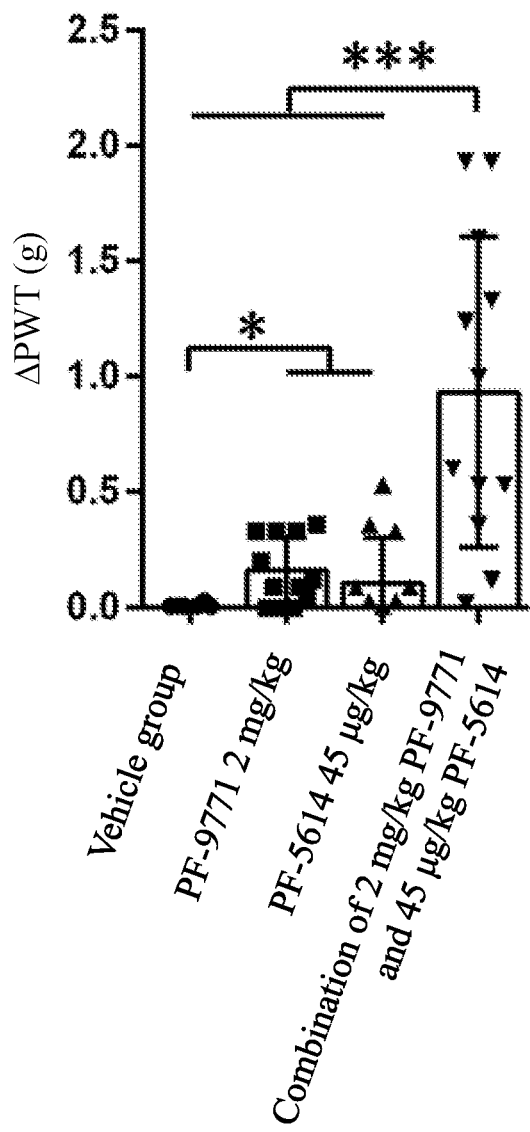
FIG. 4 demonstrates the synergistic analgesic effect of 2 mg/kg PF-05089771 and 45 µg/kg PF-04885614 (intraperitoneal injection) on mechanical pain of SNI mice at 6 weeks post operation in Example 2, where the combination of 2 mg/kg PF-05089771 and 45 µg/kg PF-04885614 is superior to the alone use of PF-05089771 or PF-04885614 in efficacy (n=12, * P<0.05, *** P<0.001, with Mann-Whitney test)
Figure 5:
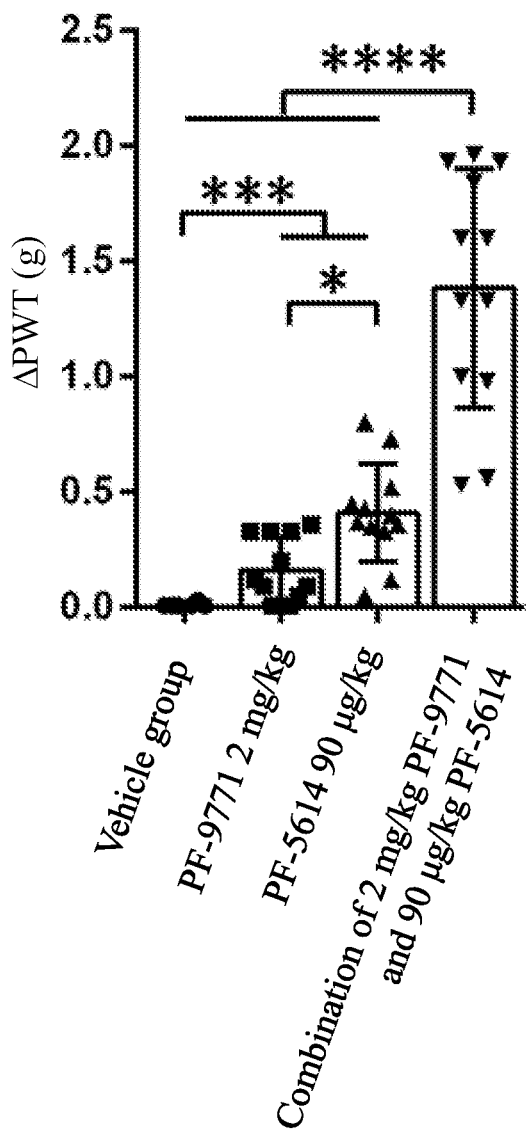
FIG. 5 demonstrates the synergistic analgesic effect of 2 mg/kg PF-05089771 and 90 µg/kg PF-04885614 (intraperitoneal injection) on mechanical pain of SNI mice at 6 weeks post operation in Example 2, where the combination of 2 mg/kg PF-05089771 and 90 µg/kg PF-04885614 is superior to the alone use of PF-05089771 or PF-04885614 in efficacy (n=12, * P<0.05, * P<0.001, ** P<0.0001, with Mann-Whitney test)
Figure 6:
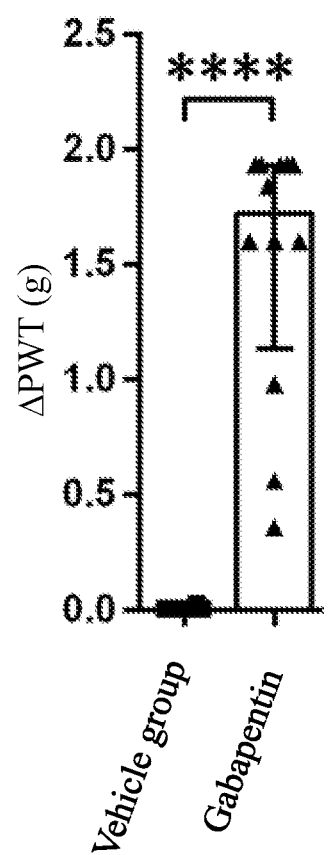
FIG. 6 demonstrates relieve effect of intraperitoneal injection of 100 mg/kg Gabapentin on mechanical pain of SNI mice at 6 weeks post operation in Example 2 (n=12, ****P<0.0001, with Mann-Whitney test)
Figure 7:
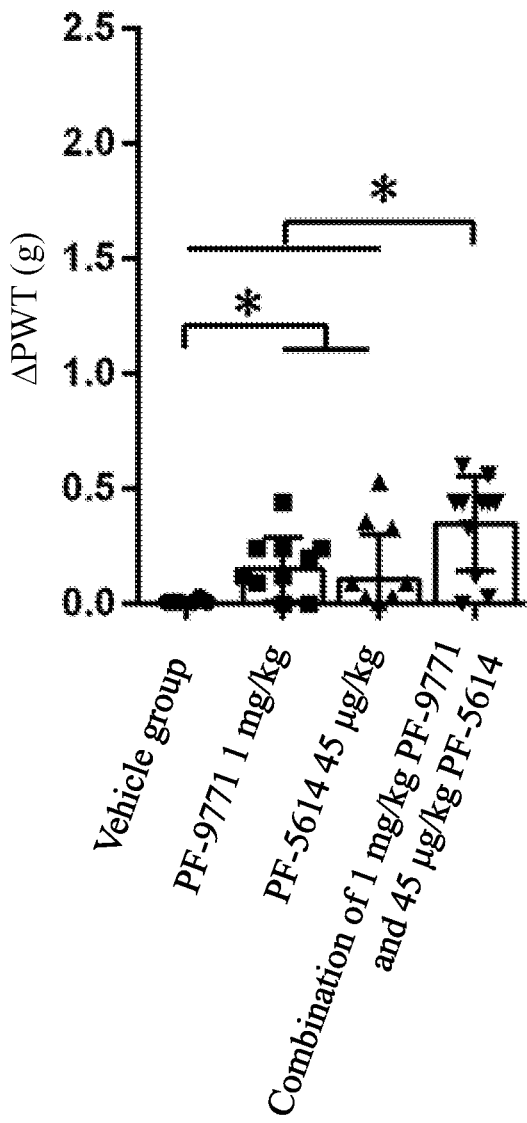
FIG. 7 demonstrates the synergistic analgesic effect of 1 mg/kg PF-05089771 and 45 µg/kg PF-04885614 (intraperitoneal injection) on mechanical pain of SNI mice at 6 weeks post operation in Example 2, where the combination of 1 mg/kg PF-05089771 and 45 µg/kg PF-04885614 is superior to the alone use of PF-05089771 or PF-04885614 (n=12, *P<0.05, with Mann-Whitney test)
Figure 8:
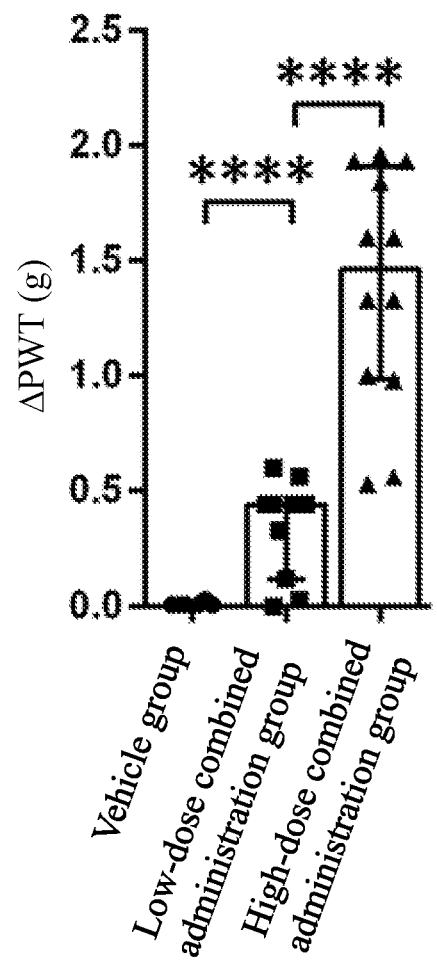
FIG. 8 demonstrates relationship between dose and analgesic effect on SNI mice in Example 2, where the analgesic effect (measured at 6 weeks post operation) of the high dose group (2 mg/kg PF-05089771 and 90 µg/kg PF-04885614) is better than that of the low-dose group (1 mg/kg of PF-05089771 and 45 µg/kg of PF-04885614) (n=11-12, ****P<0.0001, with Mann-Whitney test)

Based on Example 1, it was further found that 2/3 of the total mice (8/12, see Table 1) poorly responded (ΔPWT≤0.2 g) to 2 mg/kg PF-05089771 at 6 weeks post SNI operation, while half of them well responded to 90 µg/kg PF-04885614 (see rows 7-10 in Table 1), suggesting that the combined use of PF-05089771 and PF-04885614 might enhance the analgesic effect. It was experimentally demonstrated that the intraperitoneal injection of 2 mg/kg PF-05089771 and 45 µg/kg or 90 µg/kg PF-04885614 can significantly relieve neuropathic pain in SNI mice at 6 weeks post operation, and the analgesic effect was significantly higher than that of the single administration group, as shown in FIGS. 4-5. 100% (12/12) of the mice well responded to the combined administration of 2 mg/kg PF-05089771 and 90 µg/kg PF-04885614 (elevated threshold ΔPWT>0.5 g for each mouse), see Table 1. The efficacy of combination of PF-05089771 and PF-04885614 was equivalent to that of 100 mg/kg Gabapentin (See FIG. 6), but without sedative side effects which were caused by 100 mg/kg Gabapentin. The analgesic effect of the combination of PF-05089771 and PF-04885614 at low doses was tested. The results showed that the intraperitoneal injection of 1 mg/kg PF-05089771 and 45 µg/kg PF-04885614 could also significantly increase the mechanical pain threshold by 0.45 g, which was significantly higher than that of the single administration group, as shown in FIG. 7. Through comparative analysis, it was found that the analgesic effect of the high-dose combined administration (2 mg/kg PF-05089771 and 90 µg/kg PF-04885614) was significantly better than that of the low-dose combined administration (1 mg/kg PF-05089771 and 45 µg/kg PF-04885614). Thus, the analgesic effect of the combined administration of PF-05089771 and PF-04885614 had a dose-dependent effect, as shown in FIG. 8.

TABLE 1

Response of SNI mice to PF-05089771 and PF-04885614 at 6 weeks post operation

| 6 weeks post operation Number | PF-05089771 (2 mg/kg) ΔPWT (g) | PF-04885614 (90 µg/kg) ΔPWT (g) | PF-05089771 (2 mg/kg) + PF-04885614 (90 µg/kg) ΔPWT (g) |
|---|---|---|---|
| 1 | 0.36 | 0.36 | 0.56 |
| 2 | 0.33 | 0.53 | 1.33 |
| 3 | 0.33 | 0.53 | 1.33 |
| 4 | 0.33 | 0.53 | 1.93 |
| 5 | 0.2 | 1.6 | 1 |
| 6 | 0.05 | 0.58 | 0.98 |
| 7 | 0.09 | 0.53 | 1.93 |
| 8 | 0 | 0.44 | 1.84 |
| 9 | 0 | 0.2 | 1.6 |
| 10 | 0 | 0.2 | 1.6 |
| 11 | 0.12 | 0.12 | 1.96 |
| 12 | 0.09 | −0.03 | 0.53 |

Example 3

Figure 9:
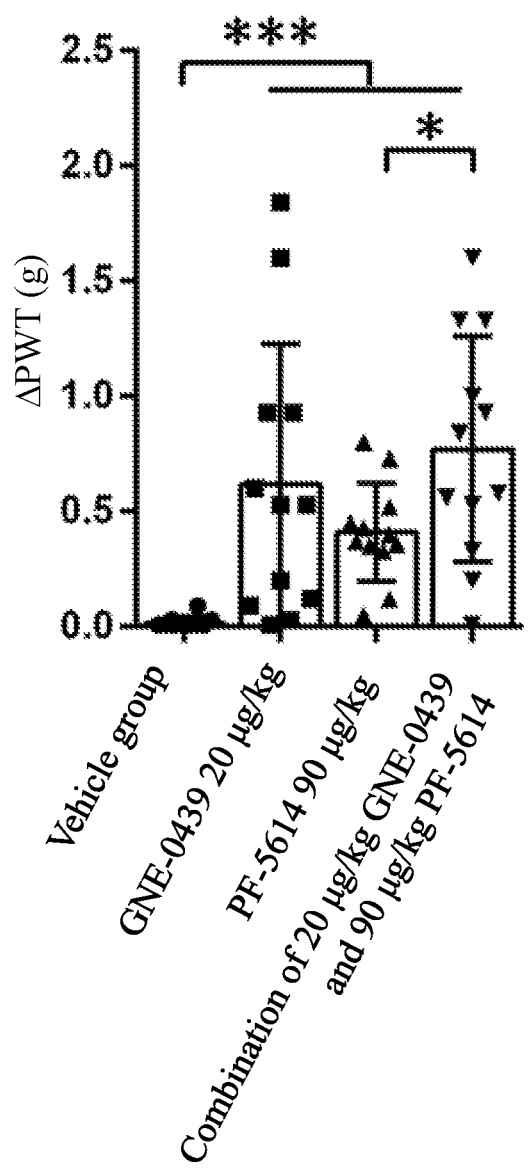
FIG. 9 shows comparison of 20 µg/kg GNE-0439, 90 µg/kg PF-04885614 and a combination thereof (intraperitoneal injection) in terms of analgesic effect on SNI mice at 6 weeks post operation in Example 3 (n=12, *P<0.05, *P<0.001, with Mann-Whitney test)
Figure 10:
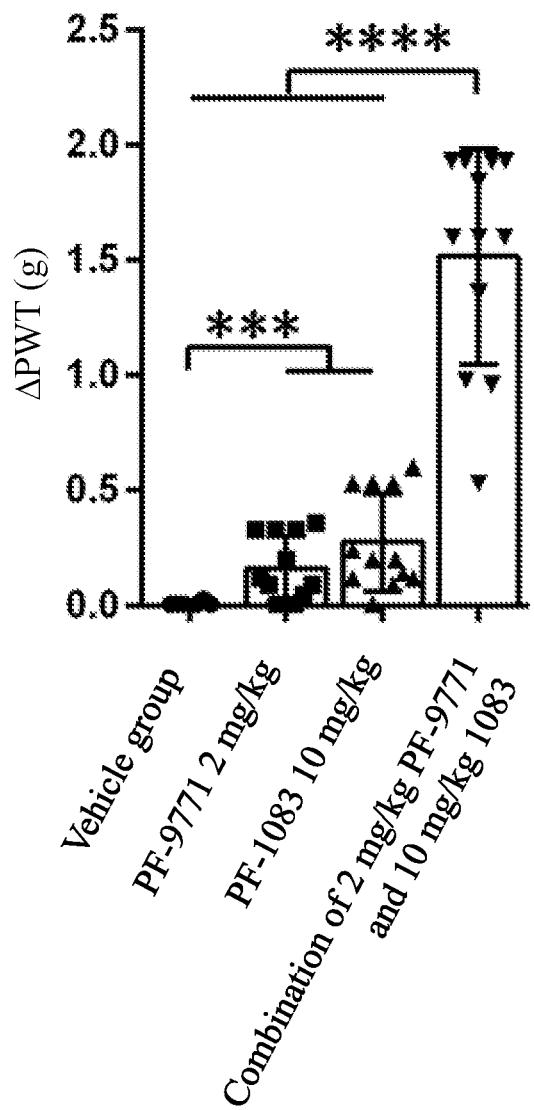
FIG. 10 shows comparison of 2 mg/kg PF-05089771, 10 mg/kg PF-04531083 and a combination thereof (intraperitoneal injection) in terms of analgesic effect on SNI mice at 6 weeks post operation (n=12, *P<0.001, ****P<0.0001, with Mann-Whitney test).

To find the optimal combination of Nav1.7 inhibitor and Nav1.8 inhibitor in terms of pain relieve effect, the combination of another Nav1.7 inhibitor GNE-0439 and PF-04885614 was tested. 20 µg/kg GNE-0439 and 90 µg/kg PF-04885614 were intraperitoneally injected into SNI mice at 6 weeks post operation. One hour later, the mechanical threshold of mice was measured using Von Frey. It was found that the analgesic effect of the co-administration of GNE-0439 and PF-04885614 was not significantly better than that of the single administration of GNE-0439 (ΔPWT=0.77+0.14 g, see FIG. 9), and was inferior to that of co-administration of 2 mg/kg PF-05089771 and 90 pg/kg PF-04885614 (ΔPWT=1.38+0.15 g). Moreover, the analgesic effect of the combination of another Nav1.8 inhibitor PF-04531083 and PF-05089771 was tested. 2 mg/kg PF-05089771 and 10 mg/kg PF-04531083 were intraperitoneally injected into SNI mice at 6 weeks post operation, and the mechanical threshold of the mice was measured using Von Frey one hour later. It was observed that the co-administration of PF-05089771 and PF-04531083 achieved better relieve effect than the single administration of PF-05089771 or PF-04885614 (see FIG. 10), but the injection of 10 mg/kg PF-04531083 will result in significant side effects such as sedation and weight loss.

What is claimed is:

1. An analgesic and antipruritic pharmaceutical composition, comprising:
PF-05089771, which is

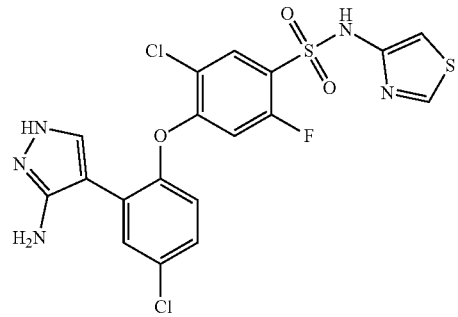 [SMILES: Nc1n[nH]cc1-c1cc(Cl)ccc1Oc1cc(F)c(S(=O)(=O)Nc2cscn2)cc1Cl]

or a salt thereof; and
PF-04885614, which is

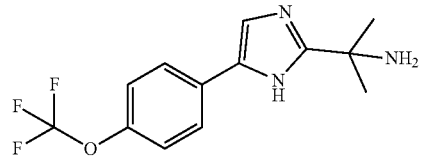 [SMILES: CC(C)(N)c1ncc(-c2ccc(OC(F)(F)F)cc2)[nH]1]

or a salt thereof.

2. The analgesic and antipruritic pharmaceutical composition of claim 1, wherein a weight ratio of the PF-05089771 to the PF-04885614 is (100-1):(1-100).

3. The analgesic and antipruritic pharmaceutical composition of claim 1, wherein a weight ratio of the PF-05089771 to the PF-04885614 is (50-1):1.

4. The analgesic and antipruritic pharmaceutical composition of claim 1, wherein a weight ratio of the PF-05089771 to the PF-04885614 is (20-30):1.

5. The analgesic and antipruritic pharmaceutical composition of claim 1, further comprising:
a pharmaceutically-acceptable carrier;

wherein the pharmaceutically-acceptable carrier is a solvent, an excipient, a dispersion medium, a coating, an iso-osmotic solution, a slow-release agent, or a combination thereof.

6. The analgesic and antipruritic pharmaceutical composition of claim 5, wherein the pharmaceutically-acceptable carrier is selected from the group consisting of starch, microcrystalline cellulose, lactose, sucrose, mannitol, inorganic salt, hydroxypropyl cellulose, sodium carboxymethyl starch, cross-linked polyvinylpyrrolidone, sodium alginate, agar, hydroxypropyl methyl cellulose, methylcellulose, hydroxyethyl cellulose, carbopol, polyvinyl alcohol, acrylic resin, chitosan, beeswax, stearic acid, and a combination thereof.

7. The analgesic and antipruritic pharmaceutical composition of claim 6, wherein the inorganic salt is selected from the group consisting of calcium sulfate, calcium hydrogen phosphate, calcium carbonate, calcium sulphate dihydrate, and a combination thereof.

8. The analgesic and antipruritic pharmaceutical composition of claim 1, wherein the analgesic and antipruritic pharmaceutical composition is for treatment of diseases which comprise pruritus and pain; wherein
the pain is inflammatory pain, neuropathic pain or a combination thereof;
the inflammatory pain is selected from the group consisting of postoperative and traumatic pain, musculoskeletal pain, menalgia, visceralgia and a combination thereof;
the musculoskeletal pain comprises arthralgia; and
the neuropathic pain is selected from the group consisting of hemicrania, odontalgia, trigeminal neuralgia, postherpetic pain, pain after spinal cord injury, sciatica, cancer-related pain, diabetic peripheral neuropathy pain, and a combination thereof.

9. The analgesic and antipruritic pharmaceutical composition of claim 1, wherein an administration route of the analgesic and antipruritic pharmaceutical composition comprises oral administration, intraoral administration, injection, respiratory administration, cutaneous administration, ophthalmic administration, nasal mucosal administration, rectal administration, vaginal administration, otic administration, or dialysis.

10. A pharmaceutical composition, comprising:
PF-05089771, which is

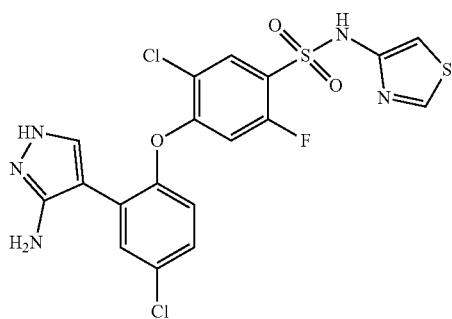 [SMILES: Nc1n[nH]cc1-c1cc(Cl)ccc1Oc1cc(F)c(S(=O)(=O)Nc2cscn2)cc1Cl]

or a salt thereof; and
PF-04885614, which is

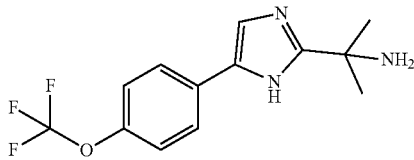 [SMILES: CC(C)(N)c1ncc(-c2ccc(OC(F)(F)F)cc2)[nH]1]

or a salt thereof;
wherein the pharmaceutical composition is for treatment of diseases in which both a voltage-gated sodium channel 1.7 ($Na_v1.7$) and a voltage-gated sodium channel 1.8 ($Na_v1.8$) are involved.

11. The pharmaceutical composition of claim 10, wherein a weight ratio of the PF-05089771 to the PF-04885614 is (100-1):(1-100).

12. The pharmaceutical composition of claim 10, wherein a weight ratio of the PF-05089771 to the PF-04885614 is (50-1):1.

13. The pharmaceutical composition of claim 10, wherein a weight ratio of the PF-05089771 to the PF-04885614 is (20-30):1.

14. The pharmaceutical composition of claim 10, further comprising:
a pharmaceutically-acceptable carrier;
wherein the pharmaceutically-acceptable carrier is a solvent, an excipient, a dispersion medium, a coating, an iso-osmotic solution, a slow-release agent, or a combination thereof.

15. The pharmaceutical composition of claim 14, wherein the pharmaceutically-acceptable carrier is selected from the group consisting of starch, microcrystalline cellulose, lactose, sucrose, mannitol, inorganic salt, hydroxypropyl cellulose, sodium carboxymethyl starch, cross-linked polyvinylpyrrolidone, sodium alginate, agar, hydroxypropyl methyl cellulose, methylcellulose, hydroxyethyl cellulose, carbopol, polyvinyl alcohol, acrylic resin, chitosan, beeswax, stearic acid, and a combination thereof.

16. The pharmaceutical composition of claim 15, wherein the inorganic salt is selected from the group consisting of calcium sulfate, calcium hydrogen phosphate, calcium carbonate, calcium sulphate dihydrate, and a combination thereof.

17. The pharmaceutical composition of claim 10, wherein the diseases comprise pruritus and pain; wherein
the pain is inflammatory pain, neuropathic pain or a combination thereof;
the inflammatory pain is selected from the group consisting of postoperative and traumatic pain, musculoskeletal pain, menalgia, visceralgia and a combination thereof;
the musculoskeletal pain comprises arthralgia; and
the neuropathic pain is selected from the group consisting of hemicrania, odontalgia, trigeminal neuralgia, postherpetic pain, pain after spinal cord injury, sciatica, cancer-related pain, diabetic peripheral neuropathy pain, and a combination thereof.

18. The pharmaceutical composition of claim 10, wherein an administration route of the pharmaceutical composition comprises oral administration, intraoral administration, injection, respiratory administration, cutaneous administration, ophthalmic administration, nasal mucosal administration, rectal administration, vaginal administration, otic administration, or dialysis.

19. A method of treating pain and itching, comprising administering to a subject in need a pharmaceutical composition, wherein the pharmaceutical composition comprises:
PF-05089771, which is

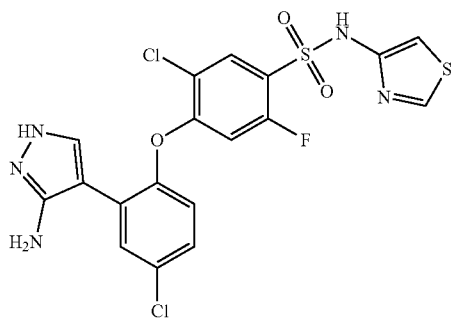 [SMILES: Nc1n[nH]cc1-c1cc(Cl)ccc1Oc1cc(F)c(S(=O)(=O)Nc2cscn2)cc1Cl]

or a salt thereof; and
PF-04885614, which is

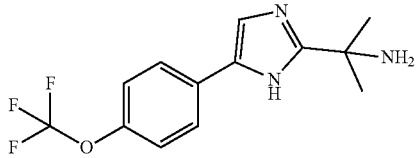 [SMILES: CC(C)(N)c1ncc(-c2ccc(OC(F)(F)F)cc2)[nH]1]

or a salt thereof.

20. The method of claim 19, wherein an administration route of the pharmaceutical composition comprises oral administration, intraoral administration, injection, respiratory administration, cutaneous administration, ophthalmic administration, nasal mucosal administration, rectal administration, vaginal administration, otic administration, or dialysis.

* * * * *